United States Patent [19]
Perronnet et al.

[11] 4,137,068
[45] Jan. 30, 1979

[54] NOVEL UREAS

[75] Inventors: Jacques Perronnet, Paris; Jean-Pierre Demoute, Montreuil-sous-Bois; Pierre Girault, Paris; André Tèche, Nanterre, all of France

[73] Assignee: Roussel Uclaf, Paris, France

[21] Appl. No.: 667,992

[22] Filed: Mar. 18, 1976

[30] Foreign Application Priority Data

Mar. 26, 1975 [FR] France .................. 75 09439

[51] Int. Cl.² ...................... A01N 9/12; C07C 119/20
[52] U.S. Cl. ........................... 71/98; 260/453 RW
[58] Field of Search ............ 71/98, 120; 260/453 RW

[56] References Cited

U.S. PATENT DOCUMENTS

| | | | |
|---|---|---|---|
| 2,655,444 | 10/1953 | Todd | 71/120 |
| 3,234,275 | 2/1966 | Malz et al. | 260/453 R |
| 3,236,624 | 2/1966 | Martin et al. | 71/120 |
| 3,276,855 | 10/1966 | Richter | 71/98 |
| 3,278,292 | 10/1966 | Johnson | 260/453 R |
| 3,344,153 | 9/1967 | Kuhle et al. | 260/453 R |
| 3,385,690 | 5/1968 | Luckenbaugh | 71/120 |
| 3,496,208 | 2/1970 | Bachman et al. | 260/453 R |
| 3,771,993 | 11/1973 | Brown | 71/98 |
| 3,946,062 | 3/1976 | Cleveland | 71/98 |
| 3,997,324 | 12/1976 | Brown | 71/98 |
| 4,043,796 | 8/1977 | Hainaut et al. | 260/453 RW |

Primary Examiner—Glennon H. Hollrah
Attorney, Agent, or Firm—Hammond & Littell

[57] ABSTRACT

Novel ureas of the formula

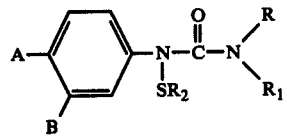

wherein A and B are chlorine or A is chlorine or hydrogen and B is —$CF_3$, R and $R_1$ are individually alkyl of 1 to 3 carbon atoms and $R_2$ is alkyl of 1 to 6 carbon atoms optionally substituted with a halogen having herbicidal properties, particularly useful in cultivated grass crops and their preparation and use.

23 Claims, No Drawings

NOVEL UREAS

STATE OF THE ART

French Pat. No. 1,339,313 and No. 1,493,603 describe urea derivatives as herbicides but not any compounds of formula I.

OBJECTS OF THE INVENTION

It is an object of the invention to provide the novel ureas of formula I and a process for their preparation.

It is another object of the invention to provide novel herbicidal compositions and to a novel method of killing weeds.

It is an additional object of the invention to provide a method of killing weeds in wheat, corn and barley crops.

These and other objects and advantages of the invention will become obvious from the following detailed description.

THE INVENTION

The novel ureas of the invention have the formula

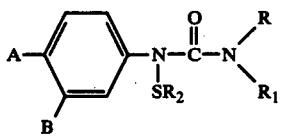
I wherein A and B are chlorine or A is chlorine or hydrogen and B is —$CF_3$, R and $R_1$ are individually alkyl of 1 to 3 carbon atoms and $R_2$ is alkyl of 1 to 6 carbon atoms optionally substituted with a halogen. Preferred are the compounds wherein R and $R_1$ are methyl.

In the compounds of formula I, R and $R_1$ may be methyl, ethyl, propyl or isopropyl and $R_2$ may be methyl, ethyl, propyl, isopropyl, linear or branched chain butyl, pentyl or hexyl, 2-chloroethyl, 3-chloropropyl or 4-chlorobutyl. Particularly preferred compounds are N-(3-trifluoromethyl phenyl)-N-isopropylthio-N',N'-dimethyl-urea, N-(3,4-dichlorophenyl)-N-isopropylthio-N',N'-dimethyl-urea and N-(3,4-dichlorophenyl)-N-ethylthio-N',N'-dimethyl-urea.

The process of the invention for the preparation of the ureas of formula I comprises reacting in the presence of a base a urea of the formula

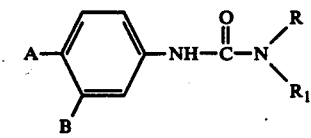
II wherein A, B, R and $R_1$ have the above definition with a sulfenyl chloride of the formula

$R_2$—S—Cl    III wherein $R_2$ has the above definition to obtain the corresponding urea of formula I.

Preferably R and $R_1$ are methyl and the reaction is effected in an organic solvent such as dimethylformamide, tetrahydrofuran, methylene chloride, chloroform, dichloroethane or any other aprotic solvent in the presence of a tertiary base such as pyridine or triethylamine. Equally useful is a strong base, preferably sodium hydride.

The sulfenyl chlorides of formula II may be made by known processes. For instance, ethane sulfenyl chloride is described by Cadogan et al, J. Chem. Soc., 1961, p. 5524 and isopropane sulfenyl chloride is described by Brintzinger et al, Ber., Vol. 87 (1954), p. 325-30. The ureas of formula II may be made by known processes. N-(3,4-dichlorophenyl)-N',N'-dimethyl-urea is described in U.S. Pat. No. 3,095,299, N-(3,4-dichlorophenyl)-N'-methyl-N'-isopropyl-urea is described in U.S. Pat. No. 2,655,444, N-(4-chloro-3-trifluoromethyl phenyl)-N',N'-dimethyl-urea is described in British Pat. No. 899,718 and N-(3-trifluoromethyl phenyl)-N',N'-dimethyl-urea is described by Wessels et al, Biochim. Biphys. Acta, Vol. 19 (1956), p. 548.

The herbicidal compositions are comprised of a herbicidally effective amount of at least one urea of formula I and an inert carrier and may contain one or more other pesticidal agents or agents for influencing the growth of plants. The compositions may be in the form of powders, granules, suspensions, emulsions or solutions. The compositions may contain anionic, cationic, or non-ionic surface active agents, inert powders such as talc, clays, silicates or kieselguhr or a vehicle such as water, alcohol, hydrocarbons or other organic solvents or a mineral, animal or vegetable oil. The compositions generally contain 5 to 90% by weight, preferably 10 to 50%, of active material.

The herbicidal compositions of the invention have a herbicidal activity entirely unexpected for its intensity. Most of the compounds are active at very low concentrations and moreover, at suitable concentration, the compositions destroy weeds in crops without attacking cultivated grasses. The compositions show a particular selectivity in killing weeds without harm to corn, wheat or barley.

The novel method of the invention for killing weeds comprises contacting weeds with an herbicidally effective amount of at least one compound of formula I. The compounds may be applied either pre-emergence or post-emergence and usually at a dose of 2 kg/hectare or less. Particularly preferred are N-(3,4-dichlorophenyl)-N-isopropylthio-N',N'-dimethyl-urea, N-(3,4-dichlorophenyl)-N-ethylthio-N', N'-dimethyl-urea and N-(3-trifluoromethyl phenyl)-N-isopropylthio-N',N'-dimethyl-urea.

In the following examples there are described several preferred embodiments to illustrate the invention. However, it should be understood that the invention is not intended to be limited to the specific embodiments.

EXAMPLE 1

N-(3,4-dichlorophenyl)-N-isopropylthio-N',N'-dimethyl-urea 7.5 g of a 50% suspension of sodium hydride in mineral oil were added in small fractions at 20° C. to a solution of 35 g of N-(3,4-dichlorophenyl)-N',N'-dimethyl-urea in 600 ml of tetrahydrofuran and the mixture was stirred for an hour at 20° C. to obtain the sodium salt of the said urea.

A current of chlorine was bubbled through a solution of 15 g of diisopropyl disulfide in 90 ml of methylene chloride cooled to −30° C. until there was an increase in weight of 7 g and after allowing the temperature to return to 0° C., the mixture was stirred for 15 minutes to obtain isopropane sulfenyl chloride in solution.

The suspension of the sodium salt of the urea was cooled to −25° C. and the solution of isopropane sulfenyl chloride cooled to −30° C. was added thereto. The mixture was stirred for 90 minutes at −25° C. and the reaction mixture was poured into a saturated aqueous sodium bicarbonate solution. The mixture was extracted with ethyl acetate and the organic extracts were washed with water, dried and evaporated to dryness. The residue was chromatographed over silica gel and elution with a 9–1 benzene-ethyl acetate mixture yielded 18 g of N-(3,4-dichlorophenyl)-N-isopropylthio-N',N'-dimethyl-urea. The IR spectrum showed absorptions at 1590 and 1560 cm$^{-1}$ characteristic of an aromatic ring and absorption at 1670 cm$^{-1}$ characteristic of carbonyl.

Analysis: $C_{12}H_{16}Cl_2N_2OS$; molecular weight = 307.24. Calculated: %C 46.91; %H 5.25; %Cl 23.08; %N 9.12; %S 10.43. Found: %C 49.6; %H 5.2; %Cl 23.3; %N 9.1; %S 10.9.

EXAMPLE 2

N-(3,4-dichlorophenyl)-N-ethylthio-N',N'-dimethyl-urea

Chlorine was bubbled through a solution of 12 g of diethyl disulfide in 90 ml of methylene chloride cooled to −40° C. until there was a weight increase of 7 g and after allowing the temperature to return to −5° C., the mixture was stirred for 5 minutes to obtain a solution of ethane sulfenyl chloride.

7.5 g of a 50% suspension of sodium hydride in mineral oil were added in small portions, to a solution of 34.9 g of N-(3,4-dichlorophenyl)-N',N'-dimethyl-urea in 600 ml of tetrahydrofuran and the mixture was stirred for an hour at 20° C. to obtain a solution of the sodium salt of the said urea.

The solution of ethane sulfenyl chloride cooled to −30° C. was poured into the solution of the sodium salt of the said urea cooled to −25° C. and the mixture was stirred for 90 minutes at −25° C. The reaction mixture was then poured into a saturated aqueous sodium bicarbonate solution and the mixture was stirred and decanted. The aqueous phase was extracted with ethyl acetate and the combined extracts were washed with water, dried and evaporated to dryness under reduced pressure. The residue was chromatographed over silica gel and elution with an 8–2 benzene-ethyl acetate mixture yielded 33 g of N-(3,4-dichlorophenyl)-N-ethylthio-N',N'-dimethyl-urea. The infrared spectrum showed absorption at 1670 cm$^{-1}$ characteristic of carbonyl and absorption at 1590, 1562 and 1475 cm$^{-1}$ characteristic of an aromatic ring.

Analysis: $C_{11}H_{14}Cl_2N_2OS$; molecular weight = 293.22 Calculated: %C 45.06 %H 4.81 %N 9.56 %Cl 24.18 %S 10.93. Found: %C 44.8; %H 4.9; %N 9.2; %Cl 24.3; %S 11.6.

EXAMPLE 3

N-(4-chloro-3-trifluoromethyl phenyl)-N-isopropylthio-N',N'-dimethyl-urea 6 g of a 50% suspension of sodium hydride in mineral oil were added in small amounts to a solution of 44 g of N-(4-chloro-3-trifluoromethyl phenyl)-N',N'-dimethyl-urea in 500 ml of tetrahydrofuran and the mixture was stirred at 20° C. for 30 minutes to obtain a solution of the sodium salt of the urea.

Chlorine was bubbled through a solution of 13.5 g of diisopropyl disulfide in 150 ml of methylene chloride cooled to −5° C. until 8 g of chlorine were absorped to obtain a solution of isopropane sulfenyl chloride.

The isopropane sulfenyl chloride solution was added at −20° C. to the solution of sodium salt of the said urea and the mixture was stirred at −5° C. for an hour and was then poured into an aqueous saturated sodium bicarbonate solution. The organic phase was separated by decanting and the aqueous phase was extracted with methylene chloride. The combined organic phases were dried and concentrated to dryness and the residue was chromatoraphed over silica gel. Elution with a 9–1 isopropyl ether-ethyl acetate mixture yielded a product which was rectified to obtain 13 g of N-(4-chloro-3-trifluoromethyl phenyl)-N-isopropylthio-N',N'-dimethyl-urea with a boiling point of 126–130° C. at 0.1 mm Hg.

Analysis: $C_{13}H_{16}ClF_3N_2OS$; molecular weight = 340.8 Calculated: %C 45.81 %H 4.73 %N 8.22 %Cl 10.40 %F 16.72 %S 9.41. Found: %C 45.9; %H 4.7; %N 7.8; %Cl 10.2; %F 16.5; %S 9.5.

IR Spectrum (chloroform):

Absorption at 1672 cm$^{-1}$ of C=O, absorption at 1606, 1577 and 1481 cm$^{-1}$ of aromatic ring and strong absorptions at 1175–1142 cm$^{-1}$ of −CF$_3$.

EXAMPLE 4

N-(3,4-dichlorophenyl)-N-(2-chloroethylthio)-N',N'-dimethyl-urea 7.2 g of a 50% suspension of sodium hydride in mineral oil were added in small amounts to a solution of 35 g of N-(3,4-dichlorophenyl)-N',N'-dimethyl-urea in 400 ml of tetrahydrofuran and the mixture was stirred for an hour to obtain a solution of the sodium salt of the said urea.

Chlorine was bubbled through a solution of 12 g of ethylene sulfide in 150 ml of methylene chloride at −40° C. until 14 g of chlorine were absorbed to obtain a solution of 2-chloroethyl sulfenyl chloride.

The solution of the sodium salt of the said urea was slowly added at −60° C. to the solution of 2-chloroethyl-sulfenyl chloride and the mixture was stirred for 15 minutes at −50° C. and was then poured into water. The mixture was extracted with ethyl acetate and the organic extracts were dried and evaporated to dryness under reduced pressure. The residue was taken up in isopropyl ether and the insolubles were removed by filtration. The filtrate was concentrated to dryness and the residue was chromatographed over silica gel. The product was eluted with a 65–35 cyclohexane-ethyl acetate mixture and was crystallized from isopropyl ether to obtain 20 g of N-(3,4-dichlorophenyl)-N-(2-chloroethylthio)-N',N'-dimethyl-urea with a melting point of <50° C. The IR spectrum (chloroform) showed absorption at 1673 cm$^{-1}$ (C=O) and at 1590, 1560 and 1450 cm$^{-1}$ (aromatic ring).

Analysis: $C_{11}H_{13}Cl_3N_2OS$; molecular weight = 327.66 Calculated: %C 40.32 %H 4.00 %N 8.55 %Cl 32.46 %S 9.78 Found: %C 40.3; %H 4.1; %N 8.4; %Cl 32.5; %S 9.8.

EXAMPLE 5

N-(3,4-dichlorophenyl)-N-(3-chloropropylthio)-N',N'-dimethyl-urea 7.2 g of a 50% suspension of sodium hydride in mineral oil were added in small portions to a solution of 35 g of N-(3,4-dichlorophenyl)-N',N'-dimethyl-urea in 350 ml of tetrahydrofuran and the mixture was stirred for an hour to obtain a solution of the sodium salt of the said urea.

Chlorine was bubbled through a solution of 21 g of di-(3-chloropropyl) disulfide in 100 ml of carbon tetrachloride until 6.8 g of chlorine were absorbed to obtain a solution of 3-chloropropane sulfenyl chloride.

The solution of the sodium salt of the said urea was slowly added at −50° C. to the solution of 3-chloropropane sulfenyl chloride and the mixture was stirred at −50° C. for 30 minutes and was then poured into a saturated aqueous sodium bicarbonate solution. The mixture was extracted with methylene chloride and the combined organic extracts were dried and evaporated to dryness. The residue was taken up in isopropyl ether and the mixture was filtered to remove insolubles. The filtrate was evaporated to dryness under reduced pressure and residue was chromatographed over silica gel. Elution with a 6-4 cyclohexane-ethyl acetate mixture yielded 16 g of N-(3,4-dichlorophenyl)-N-(3-chloropropylthio)-N',N'-dimethyl-urea.

Analysis: $C_{12}H_{15}Cl_3N_2OS$; molecular weight = 341.69 Calculated: %C 42.18 %H 4.43 %N 8.20 %Cl 31.13 %S 9.38. Found: %C 42.1; %H 4.5; %N 7.9; %Cl 30.8; %S 9.7.

RMN Spectrum:

Peaks at 2.88 ppm - hydrogens of methyl attached to nitrogen.

Peaks at 1.81, 1.93, 2.05, 2.17 and 2.28 ppm - hydrogens of methylene $\beta$ to sulfur.

Peaks at 2.95, 3.07 and 3.17 ppm — hydrogens of methylene $\alpha$ to sulfur.

Peaks at 3.53, 3.64 and 3.73 ppm — hydrogens $\alpha$ to chlorine

Peaks at 6.95, 7.0, 7.08 and 7.13 ppm — hydrogens at 6-position of aromatic ring.

Peaks at 7.35 and 7.40 ppm — hydrogen at 2 position of aromatic ring.

Peaks at 7.31 and 7.45 ppm — hydrogen at 5-position of aromatic ring.

EXAMPLE 6

N-(3,4-dichlorophenyl)-N-isopropylthio-N'-methyl-N'-isopropyl-urea 7.5 g of a 50% suspension of sodium hydride in mineral oil were added in small amounts to a solution of 39 g of N-(3,4-dichlorophenyl)-N'-methyl N'-isopropyl-urea in 400 ml of dimethylformamide and the mixture was stirred at 20° C. for an hour to obtain a solution of the sodium salt of the said urea.

Chlorine was bubbled at 0° C. through a solution of 15 g of diisopropyl disulfide in 100 ml of methylene chloride until 7 g of chlorine were absorbed to obtain a solution of isopropane sulfenyl chloride.

The latter solution was slowly added at −30° C. to the solution of the sodium salt of the urea and the mixture was stirred at −30° C. for an hour and was then poured into water. The mixture was extracted with methylene chloride and the combined organic phases were dried and evaporated to dryness. The residue was chromatographed over silica gel and was eluted with a 9-1 benzene-ethyl acetate mixture to obtain 26 g of N-(3,4-dichlorophenyl)-N-isopropylthio-N'-methyl N'-isopropyl urea.

Analysis: $C_{14}H_{20}Cl_2N_2OS$; molecular weight = 335.3 Calculated: %C 50.15; %H 6.01, %N 21.15; %Cl 8.36; %S 9.56. Found: %C 50.3; %H 6.0; %N 21.1; %Cl 8.2; %S 9.6.

EXAMPLE 7

N-(3-trifluoromethyl phenyl)-N-isopropylthio-N',N'-dimethyl-urea 7.2 g of a 50% suspension of sodium hydride in oil were added in small amounts to a solution of 34.3 g of N-(3-trifluoromethyl phenyl)-N',N'-dimethyl-urea in 680 ml of tetrahydrofuran and the mixture was stirred at 25° C. for an hour to obtain a solution of the sodium of the said urea.

Chlorine was bubbled at 0° C. through a solution of 15 g of diisopropyl disulfide in 100 ml of methylene chloride until 7 g of chlorine were absorbed to obtain a solution of isopropane sulfenyl chloride.

The latter solution was slowly added at −30° C. to the solution of the sodium salt of the said urea and the mixture was stirred at −35° C. for an hour and was then poured into a saturated aqueous sodium bicarbonate solution. The mixture was extracted with ethyl acetate and the combined organic extracts were dried and evaporated to dryness. The residue was chromatographed over silica gel, eluted with an 8-2 benzene-ethyl acetate mixture and was rectified to obtain 23 g of N-(3-trifluoromethyl phenyl)-N-isopropylthio-N',N'-dimethyl-urea with a boiling point of 97° C. at 0.1 mm Hg and a refractive index of $N_D^{20}$ = 1.5050. The IR spectrum (chloroform) showed absorption at 1670 cm$^{-1}$ (C=O) and 1612, 1593 and 1490 cm$^{-1}$ (aromatic ring).

Analysis: $C_{13}H_{17}F_3N_2OS$; molecular weight = 307.35 Calculated: %C 50.96 %H 5.60 %F 18.61 %N 9.15 %S 10.46 Found: %C 50.9; %H 5.4; %F 18.5; %N 9.1; %S 10.7;

EXAMPLE 8

N-(3,4-dichlorophenyl)-N-n-butylthio-N',N'-dimethyl-urea 7.2 g of a 50% suspension of sodium hydride in oil were added at 20° C. in small portions to a solution of 35 g of N-(3,4-dichlorophenyl)-N',N'-dimethyl-urea in 400 ml of tetrahydrofuran and the mixture was stirred for 30 minutes to obtain a solution of the sodium salt of the said urea.

Chlorine was bubbled at −5° C. through a solution of 26.7 g of di-n-butyl disulfide in 90 ml of methylene chloride until 9.5 g of chlorine were absorbed to obtain a solution of n-butane sulfenyl chloride.

The latter solution was slowly added at 20° C. to the solution of the sodium salt of the urea and the mixture was stirred for 15 minutes and was then poured into an aqueous sodium bicarbonate solution. The mixture was extracted with methylene chloride and the extracts were dried and evaporated to dryness. The residue was chromatographed over silica gel and was eluted with a 9-1 benzene-ethyl acetate mixture to obtain 20 g of raw N-(3,4-dichlorophenyl)-N-n-butylthio-N',N'-dimethyl-urea.

IR Spectrum (chloroform):

Absorption at 1670 cm$^{-1}$ (C=O) and at 1590, 1560 and 1475 cm$^{-1}$ (aromatic ring).

RMN Spectrum

Peak at 0.86 ppm — hydrogens of methyl of n-butyl

Peak at 1.47 ppm — hydrogens of methylene in n-butyl $\beta$ and $\gamma$ to sulfur.

Peak at 2.89 ppm — hydrogens of methyl attached to nitrogen

Peak at 2.98 ppm — hydrogens of methylene in n-butyl $\alpha$ to sulfur.

Peaks at 6.94, 6.97, 7.09 and 7.12 ppm — hydrogens in 6-position of aromatic ring Peaks at 7.27 and 7.41 ppm — hydrogens in 5-position of aromatic ring.

Peaks at 7.34 and 7.37 ppm — hydrogens in 2-position of aromatic ring.

EXAMPLE 9

A wettable powder was prepared consisting of 25% by weight of N-(3-trifluoromethyl phenyl)-N-isopropylthio-N',N'-dimethyl-urea or N-(3,4-dichlorophenyl)-N-isopropylthio-N',N'-dimethyl-urea, 10% by weight of Ekapersol S (condensation product of sodium naphthalene sulfonate), 0.5% by weight of Brecolane NVA (sodium alkyl naphthalene sulfonate), 34.5% by weight of Zeosil 39 (precipitated synthetic hydrated silica) and 30% by weight of Vercoryl S (colloidal kaolin) which could be mixed with water for spraying.

EXAMPLE 10

An emulsifiable herbicide concentrate was prepared consisting of 25% by weight of N-(3,4-dichlorophenyl)-N-ethylthio-N',N'-dimethyl-urea, 6.4% by weight of Atlox 4851 (mixture of alkyl arylsulfonate + polyoxyethylene triglyceride with a viscosity of 300–700 cps at 25° C.), 3.2% by weight of Atlox 4855 (mixture of alkyl arylsulfonate + polyoxyethylene triglyceride with a viscosity of 1500–1900 cps at 25° C. and 64.4% by weight of xylene which could be diluted with water before spraying to obtain the desired concentration of the active material.

HERBICIDAL DATA

The test plants were grown in a culture flat (23 × 14 × 4 cm) having a double bottom and means for watering from below. The species were placed into a single flat at a ratio of 20 seeds per species, in rows spaced 3 cm apart. There were four sets of flats for each compound and concentration. The growing conditions were: temperature 20± C. ≠ 2° C., humidity about 60%, lighting by a fluorescent tube (day light + brilliant white) from 6 hours to 22 hours each day. The soil mixture was composed of 10 volumes of earth, 10 volumes of river sand and 2 volumes of peat.

For the pre-emergence tests, the herbicidal treatment was carried out 24 hours after the seeds had been planted and the first watering was effected by sprinkling to carry a part of the product to the seed level. The post-emergence tests were effected by 21 days after the seeds had been planted, on the aerial parts. The test products were each applied under standard conditions with the aid of a microsprayer at doses of 5, 2.5, 1.25, 0.625, 0.312 and 0.156 kg/ha and at a dilution of 560 l/ha. Control tests without treatment were carried out in the same way. The final controls were effected by number of the plants 21 days after treatment. The results were expressed as a percentage of reduction of the number of plants (Mortality) M.

$$M = \frac{\text{Number of control plants} - \text{Number of treated plants}}{\text{Number of control plants}} \times 100$$

The compounds used were N-(3-trifluoromethyl phenyl)-N-isopropylthio-N',N'-dimethyl-urea [compound A], N-(3,4-dichlorophenyl)-N-isopropylthio-N',N'-dimethyl-urea [compound B] and N-(3,4-dichlorophenyl)-N-ethylthio-N',N'-dimethyl-urea [compound C].

| Treated Plants | Pre-emergence - Compound A Doses in Kg/ha | | | | Post-emergence - Compound A Doses in Kg/ha | | | |
|---|---|---|---|---|---|---|---|---|
| | 5 | 2.5 | 1.25 | 0.625 | 5 | 2.5 | 1.25 | 0.625 |
| Triticum sativum | 0 | 0 | 0 | 0 | 72 | 64 | 37 | 68 |
| Hodeum Spec | 0 | 0 | 0 | 0 | 0 | 0 | 0 | 0 |
| Zea Mays | 0 | 0 | 0 | 0 | 65 | 33 | 0 | 0 |
| Avena Fatua | 60 | 60 | 40 | 32 | 100 | 76 | 20 | 0 |
| Agrostis Tenuis | 100 | 100 | 100 | 100 | 100 | 100 | 100 | 88 |
| Lolium Perenne | 100 | 100 | 100 | 62 | 100 | 100 | 15 | 0 |
| Alopecurus Myosuroides | 100 | 100 | 100 | 65 | 100 | 100 | 0 | 0 |
| Beta Vulgaris | 100 | 100 | 100 | 100 | 100 | 100 | 100 | 100 |
| Chenopodium Quinoa | 100 | 100 | 100 | 100 | 100 | 100 | 100 | 100 |
| Chrysanthemum Coronarium | 100 | 100 | 100 | 100 | 100 | 100 | 100 | 100 |
| Galium Aparine | 59 | 77 | 27 | 0 | 100 | 100 | 93 | 57 |
| Sinapis Alba | 100 | 100 | 100 | 100 | 100 | 100 | 100 | 100 |
| Rumex Crispus | 100 | 100 | 100 | 100 | 100 | 100 | 100 | 100 |
| Trifolium Praetense | 100 | 100 | 100 | 100 | 100 | 100 | 100 | 100 |

| Treated plants | Pre-emergence - compound B Doses in Kg/ha | | | |
|---|---|---|---|---|
| | 5 | 2.5 | 1.25 | 0.625 |
| Triticum Sativum | 100 | 95 | 46 | 0 |
| Hordeum Spec | 100 | 100 | 62 | 51 |
| Zea Mays | 31 | 46 | 46 | 0 |
| Avena Fatua | 100 | 100 | 69 | 54 |
| Agrostis Tenuis | 100 | 100 | 100 | 84 |
| Lolium Perenne | 100 | 100 | 100 | 94 |
| Alopecurus Myosuroides | 100 | 100 | 31 | 46 |
| Beta Vulgaris | 100 | 100 | 100 | 100 |
| Chenopodium Chinoa | 100 | 100 | 100 | 100 |
| Chrysanthemum Coronarium | 100 | 100 | 100 | 100 |
| Galium Aparine | 100 | 100 | 80 | 49 |
| Sinapis Alba | 100 | 100 | 100 | 100 |
| Rumex Crispus | 100 | 100 | 100 | 100 |
| Trifolium Praetense | 100 | 100 | 100 | 100 |

| Treated Plants | Post-emergence compound B Doses in Kg/ha | | | | | |
|---|---|---|---|---|---|---|
| | 5 | 2.5 | 1.25 | 0.625 | 0.312 | 0.156 |
| Triticum Sativum | 100 | 100 | 39 | 0 | 0 | 0 |
| Hordeum Spec | 100 | 68 | 29 | 0 | 0 | 0 |
| Zea Mays | 71 | 73 | 33 | 18 | 0 | 0 |

-continued

| Treated Plants | Post-emergence compound B Doses in Kg/ha | | | | | |
|---|---|---|---|---|---|---|
| | 5 | 2.5 | 1.25 | 0.625 | 0.312 | 0.156 |
| Avena Fatua | 100 | 100 | 68 | 0 | 0 | 0 |
| Agrostis Tenuis | 100 | 100 | 100 | 100 | 100 | 100 |
| Lolium Perenne | 100 | 100 | 100 | 100 | 100 | 100 |
| Alopecurus Myosuroides | 100 | 100 | 100 | 22 | 20 | 34 |
| Beta Vulgaris | 100 | 100 | 100 | 100 | 100 | 81 |
| Chenopodium Chinoa | 100 | 100 | 100 | 100 | 100 | 100 |
| Chrysanthemum Coronarium | 100 | 100 | 100 | 100 | 100 | 100 |
| Galium Aparine | 100 | 100 | 100 | 100 | 89 | 40 |
| Sinapis Alba | 100 | 100 | 100 | 100 | 100 | 100 |
| Rumex Crispus | 100 | 100 | 100 | 100 | 100 | 100 |
| Trifolium Praetense | 100 | 100 | 100 | 100 | 100 | 92 |

| Treated Plants | Pre-emergence - Compound C Doses in Kg/ha | | | |
|---|---|---|---|---|
| | 5 | 2.5 | 1.25 | 0.625 |
| Triticum Sativum | 84 | 95 | 70 | 0 |
| Hordeum Spec | 100 | 100 | 86 | 22 |
| Zea Mays | 23 | 23 | 0 | 0 |
| Avena Fatua | 100 | 100 | 100 | 27 |
| Agrostis Tenuis | 100 | 100 | 100 | 84 |
| Lolium Perenne | 100 | 100 | 100 | 92 |
| Alopecurus Myosuroides | 100 | 100 | 100 | 0 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 100 | 100 | 82 | 44 |
| Sinapis Alba | 100 | 100 | 100 | 100 |
| Rumex Crispus | 100 | 100 | 100 | 100 |
| Trifolium Praetense | 100 | 100 | 100 | 100 |

| Treated plants | Post-emergence - compound C Doses in Kg/ha | | | | | |
|---|---|---|---|---|---|---|
| | 5 | 2.5 | 1.25 | 0.625 | 0.312 | 0.156 |
| Triticum Sativum | 100 | 100 | 0 | 0 | 0 | 0 |
| Hordeum Spec | 100 | 68 | 0 | 0 | 0 | 0 |
| Zea Mays | 80 | 50 | 0 | 0 | 0 | 0 |
| Avena Fatua | 100 | 100 | 68 | 18 | 0 | 0 |
| Agrostis Tenuis | 100 | 100 | 100 | 100 | 100 | 100 |
| Lolium Perenne | 100 | 100 | 100 | 100 | 100 | 100 |
| Alopecurus Myosuroides | 100 | 100 | 100 | 43 | 66 | 0 |
| Beta Vulgaris | 100 | 100 | 100 | 100 | 100 | 100 |
| Chenopodium Chinoa | 100 | 100 | 100 | 100 | 100 | 100 |
| Chrysantheumum Coronarium | 100 | 100 | 100 | 100 | 100 | 100 |
| Galium Aparine | 100 | 100 | 100 | 100 | 100 | 100 |
| Sinapis Alba | 100 | 100 | 100 | 100 | 100 | 100 |
| Rumex Crispus | 100 | 100 | 100 | 100 | 100 | 100 |
| Trifolium Praetense | 100 | 100 | 100 | 100 | 100 | 100 |

Compound A and especially compounds B and C have a particularly intense herbicidal activity and at the useful concentrations, the compounds destroy weeds without attacking the cultivated gramineous plants.

Various modifications of the products and processes of the invention may be made without deaparting from the spirit or scope thereof and it should be understood that the invention is intended to be limited only as defined in the appended claims.

We claim:

1. A compound of the formula

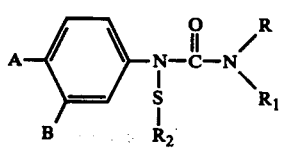

wherein A and B may be chlorine and when B is trifluoromethyl, A is selected from the group consisting of hydrogen and chlorine, R and $R_1$ are individually alkyl of 1 to 3 carbon atoms and $R_2$ is alkyl of 1 to 6 carbon atoms optionally substituted with a chlorine.

2. A compound of claim 1 wherein R and $R_1$ are methyl.

3. A compound of claim 1 which is N-(3,4-dichlorophenyl)-N-isopropylthio-N',N'-dimethyl-urea.

4. A compound of claim 1 which is N-(3,4-dichlorophenyl)-N-ethylthio-N',N'-dimethyl-urea.

5. A compound of claim 1 which is N-(3,4-dichlorophenyl)-N-2-chloroethylthio-N',N'-dimethyl-urea.

6. A compound of claim 1 which is N-(3,4-dichlorophenyl)-N-3-chloropropylthio-N',N'-dimethyl-urea.

7. A compound of claim 1 which is N-(3,4-dichlorophenyl)-N-n-butylthio-N',N'-dimethyl-urea.

8. A compound of claim 1 which is N-(3-trifluoromethyl phenyl)-N-isopropylthio-N',N'-dimethyl-urea.

9. A compound of claim 1 which is N-(4-chloro-3-trifluoromethyl phenyl)-N-isopropylthio-N',N'-dimethyl-urea.

10. A compound of claim 1 which is N-(3,4-dichlorophenyl)-N-isopropylthio-N'-methyl N'-isopropyl-urea.

11. A herbicidal composition comprising a herbicidally effective amount of a compound of claim 1 and an inert carrier.

12. A composition of claim 11 wherein R and $R_1$ are methyl.

13. A method of killing weeds which comprises contacting weeds with a herbicidally effective amount of a compound of claim 1.

14. The method of claim 13 wherein R and $R_1$ are methyl.

15. The method of claim 13 wherein the active compound is applied to fields at a rate of not more than 2 kg/hectare.

16. The method of claim 15 wherein the active compound is N-(3-trifluoromethyl phenyl)-N-isopropylthio-N',N'-dimethyl-urea.

17. The method of claim 15 wherein the active compound is N-(3,4-dichlorophenyl)-N-isopropylthio-N',N'-dimethyl-urea.

18. The method of claim 15 wherein the active compound is N-(3,4-dichlorophenyl)-N-ethylthio-N',N'-dimethyl-urea.

19. A method of selectively killing weeds in gramineous crops comprising applying to gramineous crops a herbicidally effective amount of a compound of claim 1.

20. The method of claim 19 wherein the crops are wheat, barley or corn.

21. The method of claim 20 wherein the active product is N-(3-trifluoromethyl phenyl)-N-isopropylthio-N',N'-dimethyl-urea.

22. The method of claim 20 wherein the active compound is N-(3,4-dichlorophenyl)-N-isopropylthio-N',N'-dimethyl-urea.

23. The method of claim 20 wherein the active compound is N-(3,4-dichlorophenyl)-N-ethylthio-N',N'-dimethyl-urea.

* * * * *